(12) United States Patent
Jiang et al.

(10) Patent No.: US 10,546,192 B2
(45) Date of Patent: Jan. 28, 2020

(54) DEVICE AND METHOD FOR RECOGNIZING FINGERPRINT

(71) Applicant: Beijing Xiaomi Mobile Software Co., Ltd., Beijing (CN)

(72) Inventors: Zhongsheng Jiang, Beijing (CN); Chuanshun Ji, Beijing (CN); Gang Wang, Beijing (CN)

(73) Assignee: Beijing Xiaomi Mobile Software Co., Ltd., Beijing (CN)

( * ) Notice: Subject to any disclaimer, the term of this patent is extended or adjusted under 35 U.S.C. 154(b) by 182 days.

(21) Appl. No.: 15/636,937

(22) Filed: Jun. 29, 2017

(65) Prior Publication Data
US 2018/0005030 A1 Jan. 4, 2018

(30) Foreign Application Priority Data
Jun. 30, 2016 (CN) .......................... 2016 1 0511858

(51) Int. Cl.
*G06K 9/28* (2006.01)
*G06K 9/00* (2006.01)
*A61B 5/1172* (2016.01)

(52) U.S. Cl.
CPC ........ *G06K 9/00563* (2013.01); *A61B 5/1172* (2013.01); *G06K 9/0004* (2013.01);
(Continued)

(58) Field of Classification Search
CPC ... G06K 9/00013–0012; G06K 9/00006–0012
See application file for complete search history.

(56) References Cited

U.S. PATENT DOCUMENTS

| 7,508,964 B2 | 3/2009 | Hamid |
| 8,125,517 B2 | 2/2012 | Oguchi |

(Continued)

FOREIGN PATENT DOCUMENTS

| CN | 103271739 A | 9/2013 |
| CN | 203366416 U | 12/2013 |

(Continued)

OTHER PUBLICATIONS

Hwang et al., "Epidermal Differential Impedance Sensor for Conformal Skin Hydration Monitoring", Biointerphasis (2012) 7:52, published by the American Vacuum Society, cover page and pp. 1-9. (Year: 2012).*

(Continued)

*Primary Examiner* — Brian Werner
(74) *Attorney, Agent, or Firm* — Finnegan, Henderson, Farabow, Garrett & Dunner, L.L.P.

(57) ABSTRACT

A device for recognizing a fingerprint, includes: a fingerprint sensor; at least two moisture detection electrodes disposed within a preset range of the fingerprint sensor; and a processing module coupled to the fingerprint sensor and the at least two moisture detection electrodes. The fingerprint sensor is configured to output a fingerprint signal to the processing module when a user touches the fingerprint sensor and the at least two moisture detection electrodes with a finger. The processing module is configured to acquire a characteristic value which is positively related to an impedance between the at least two moisture detection electrodes when the user touches the fingerprint sensor and the at least two moisture detection electrodes with the finger; determine a fingerprint recognition parameter which matches the characteristic value; and perform fingerprint recognition according to the determined fingerprint recognition parameter and the fingerprint signal.

14 Claims, 7 Drawing Sheets

(52) U.S. Cl.
CPC ....... *G06K 9/0012* (2013.01); *G06K 9/00013* (2013.01); *G06K 9/00053* (2013.01); *G06K 9/00087* (2013.01)

(56) References Cited

U.S. PATENT DOCUMENTS

| | | | | |
|---|---|---|---|---|
| 9,576,179 | B2* | 2/2017 | Bae | G06K 9/00013 |
| 2007/0003110 | A1 | 1/2007 | Gutta et al. | |
| 2008/0013806 | A1* | 1/2008 | Hamid | G06K 9/00013 |
| | | | | 382/124 |
| 2014/0341448 | A1 | 11/2014 | Chiu | |
| 2015/0023571 | A1 | 1/2015 | Gozzini et al. | |
| 2015/0146944 | A1 | 5/2015 | Pi et al. | |
| 2017/0262720 | A1* | 9/2017 | Hwang | G06K 9/0002 |
| 2017/0323137 | A1* | 11/2017 | Andersson | G06K 9/209 |

FOREIGN PATENT DOCUMENTS

| | | |
|---|---|---|
| CN | 103942538 A | 7/2014 |
| CN | 204360392 U | 5/2015 |
| CN | 105205464 A | 12/2015 |
| CN | 105404875 A | 3/2016 |
| CN | 106203303 A | 12/2016 |
| EP | 2 983 109 A2 | 2/2016 |
| JP | H10-302047 A | 11/1988 |
| JP | H11-309133 A | 11/1999 |
| JP | 2002-163655 A | 6/2002 |
| JP | 2003-187234 A | 7/2003 |
| JP | 2005-110991 A | 4/2005 |
| JP | 2007-264958 A | 10/2007 |
| JP | 2012-168662 A | 9/2012 |
| JP | 2016038913 A | 3/2016 |
| RU | 22429250 C2 | 3/2005 |
| WO | WO 2015/134816 A1 | 9/2015 |
| WO | WO 2016/043645 A1 | 3/2016 |

OTHER PUBLICATIONS

English translation of International Search Report issued by the State Intellectual Property Office of the People's Republic of China (SIPO) dated Mar. 1, 2017, in counterpart International Application No. PCT/CN2016/110981.

Extended European Search Report issued by European Patent Office dated Nov. 9, 2017, in counterpart European Application No. 17179139.5-1901.

International Search Report issued by the State Intellectual Property Office of the People's Republic of International (SIPO) dated Mar. 1, 2017, in counterpart International Application No. PCT/CN2016/110981.

* cited by examiner

DEVICE AND METHOD FOR RECOGNIZING FINGERPRINT

CROSS-REFERENCE TO RELATED APPLICATIONS

This application is based upon and claims priority to Chinese Patent Application No. 201610511858.3, filed on Jun. 30, 2016, the entire contents thereof are incorporated herein by reference.

TECHNICAL FIELD

The present disclosure generally relates to the field of information technology, and more particularly, to a device and a method for recognizing a fingerprint.

BACKGROUND

A fingerprint generally remains unchanged throughout one's life and has uniqueness, and different users have different fingerprints. Due to this reason, with development of information technology, fingerprint recognition technology has found wide application usually in fields such as identity verification.

A device for recognizing a fingerprint generally includes a fingerprint sensor and a processing module. When a user touches the fingerprint sensor with a finger, the fingerprint sensor may acquire a fingerprint signal according to a texture feature of the finger. The fingerprint sensor may send the fingerprint signal to the processing module. Then, the processing module may generate a fingerprint image according to the fingerprint signal, extract features from the fingerprint image, and match the extracted feature information with previously stored feature information, to recognize the fingerprint.

SUMMARY

According to a first aspect of the present disclosure, a device for recognizing a fingerprint is provided. The device includes a fingerprint sensor; at least two moisture detection electrodes disposed within a preset range of the fingerprint sensor; and a processing module coupled to the fingerprint sensor and the at least two moisture detection electrodes. The fingerprint sensor is configured to output a fingerprint signal to the processing module when a user touches the fingerprint sensor and the at least two moisture detection electrodes with a finger. The processing module is configured to acquire a characteristic value when the user touches the fingerprint sensor and the at least two moisture detection electrodes with the finger, the characteristic value being positively related to an impedance between the at least two moisture detection electrodes; determine a fingerprint recognition parameter which matches the characteristic value; and perform fingerprint recognition according to the determined fingerprint recognition parameter and the fingerprint signal.

According to a second aspect of the present disclosure, a method for recognizing a fingerprint is provided. The method is applied in a device including: a fingerprint sensor, at least two moisture detection electrodes, and a processing module. The method includes acquiring a characteristic value and a fingerprint signal when a user touches the fingerprint sensor and the at least two moisture detection electrodes with a finger, the characteristic value being positively related to an impedance between the at least two moisture detection electrodes; determining a fingerprint recognition parameter which matches the characteristic value; and performing fingerprint recognition according to the determined fingerprint recognition parameter and the fingerprint signal.

According to a third aspect of the present disclosure, a non-transitory computer-readable storage medium is provided. The storage medium stores instructions that, when executed by a processor in a terminal, cause the terminal to perform a method for recognizing a fingerprint. The method includes: acquiring a characteristic value and a fingerprint signal when the user touches the fingerprint sensor and the at least two moisture detection electrodes with a finger, the characteristic value being positively related to an impedance between the at least two moisture detection electrodes; determining a fingerprint recognition parameter which matches the characteristic value; and performing fingerprint recognition according to the determined fingerprint recognition parameter and the fingerprint signal.

It is to be understood that both the foregoing general description and the following detailed description are exemplary only and are not restrictive of the present disclosure.

BRIEF DESCRIPTION OF THE DRAWINGS

The accompanying drawings, which are incorporated in and constitute a part of this specification, illustrate embodiments consistent with the invention and, together with the description, serve to explain the principles of the invention.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the present disclosure. Instead, they are merely examples of apparatuses and methods consistent with aspects related to the present disclosure as recited in the appended claims.

Figure 1:
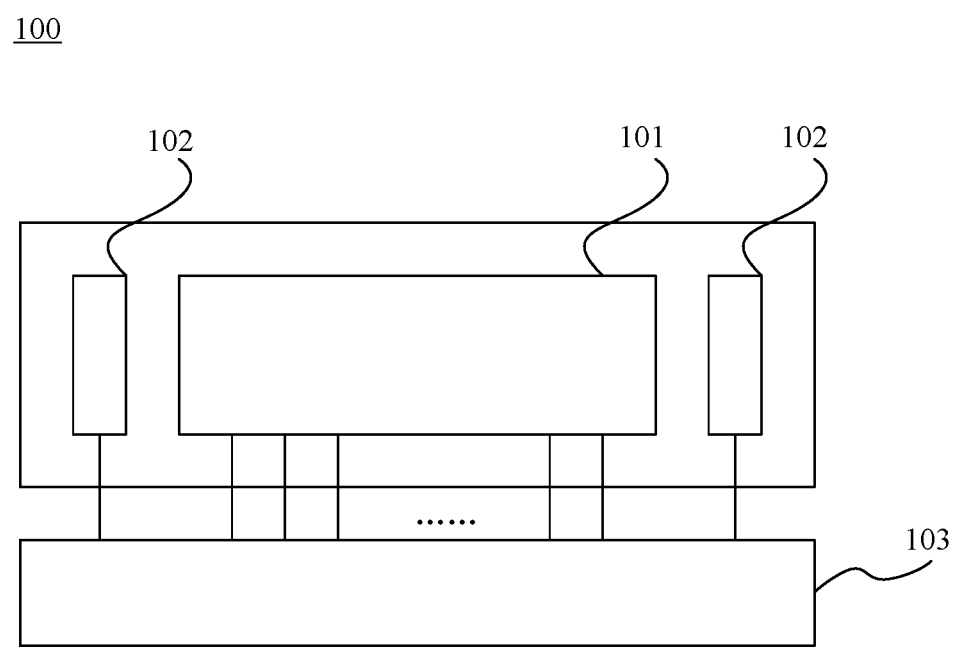
FIG. 1 is a block diagram of a device for recognizing a fingerprint according to an exemplary embodiment.

FIG. 1 is a block diagram of a device 100 for recognizing a fingerprint according to an exemplary embodiment. The device 100 for recognizing a fingerprint may realize a function of recognizing a fingerprint, and may be applied in a device such as a mobile phone, a tablet computer, an access control device, and so on, which will not be limited by the present embodiment.

As shown in FIG. 1, the device 100 includes a fingerprint sensor 101, at least two moisture detection electrodes 102, and a processing module 103.

In an embodiment, the fingerprint sensor 101 is coupled to the processing module 103. When a user touches the fingerprint sensor 101 with a finger, the fingerprint sensor 101 may output a fingerprint signal to the processing module 103, and the processing module 103 may perform fingerprint recognition according to the fingerprint signal.

Figure 2:
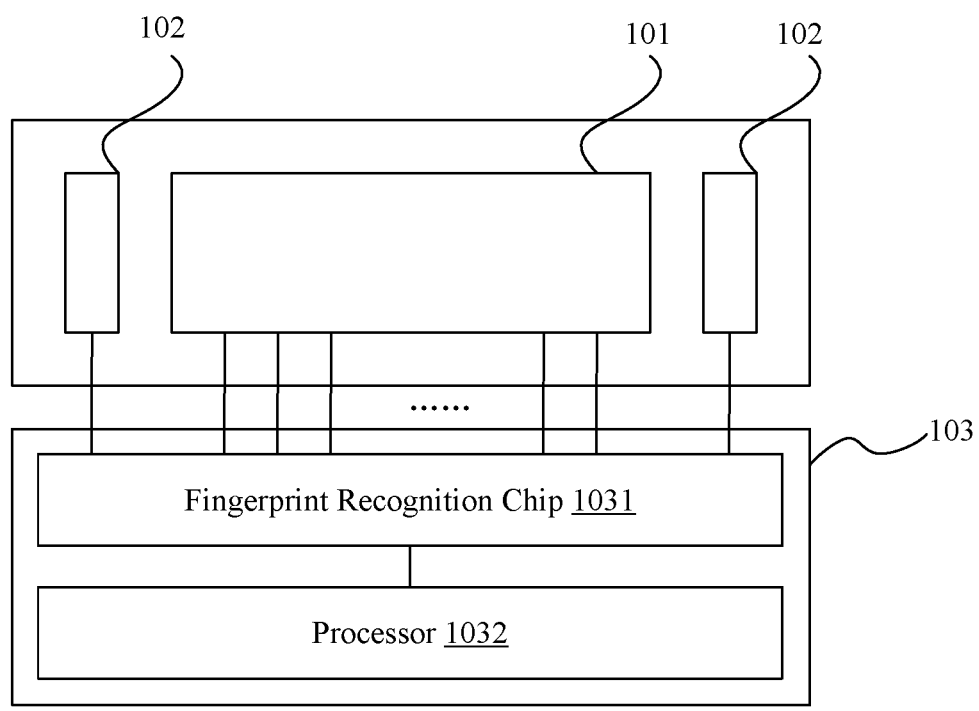
FIG. 2 is a block diagram of a device for recognizing a fingerprint according to an exemplary embodiment.

Referring to FIG. 2, the processing module 103 may include a fingerprint recognition chip 1031 and a processor 1032. The processor 1032 may be a central processor or other device which has processing capability. The fingerprint recognition chip 1031 may be coupled to the processor 1032, and configured to control the fingerprint sensor 101 to scan a finger of a user to obtain a fingerprint signal. Then, the fingerprint recognition chip 1031 may send the fingerprint signal to the processor 1032, and the processor 1032 may recognize the fingerprint according to the fingerprint signal.

The fingerprint sensor 101 may be disposed on a surface of a housing of the device 100 for recognizing a fingerprint, such that a user may touch the fingerprint sensor 101 with a finger. The at least two moisture detection electrodes 102 may also be located on a surface of the housing of the device 100 for recognizing a fingerprint, and may be located within a preset range of the fingerprint sensor 101, for example, adjacent to the fingerprint sensor 101. When a user touches the fingerprint sensor 101 with a finger, the user may also touch the at least two moisture detection electrodes 102.

In an embodiment, the preset range may be within a preset distance to the center of the fingerprint sensor 101. The preset distance may be determined according to a size of the user's finger. A shape of the preset range may be a rectangular shape, a circular shape or other shape, as long as it allows the user to touch the at least two moisture detection electrodes 102 while touching the fingerprint sensor 101.

In addition, the at least two moisture detection electrodes 102 may be coupled to the processing module 103, and configured to detect the moisture of the user's finger (for example, the amount of water or other liquid present on the user's finger). When the user touches the at least two moisture detection electrodes 102 with a finger, an impedance will be generated between the at least two moisture detection electrodes 102. The value of the impedance depends on the moisture of the user's finger. At this time, the processing module 103 may acquire a characteristic value indicating the impedance value between the at least two moisture detection electrodes 102, and the characteristic value is positively related to the impedance value. Therefore, the characteristic value may also represent the moisture of the user's finger. The larger the moisture of the user's finger is, the smaller the impedance value between at least two moisture detection electrodes 102 will be, and the smaller the characteristic value will be. On the contrary, the smaller the moisture of the user's finger is, the larger the impedance value between at least two moisture detection electrodes 102 will be, and the larger the characteristic value will be.

In the embodiment, when the user touches the fingerprint sensor 101 and the at least two moisture detection electrode 102 with a finger, the fingerprint sensor 101 may output a fingerprint signal to the processing module 103. The processing module 103 may acquire the fingerprint signal outputted by the fingerprint sensor 101 and acquire the characteristic value to determine a fingerprint recognition parameter which matches the characteristic value. The processing module 103 may perform fingerprint recognition according to the determined fingerprint recognition parameter and the fingerprint signal.

In an embodiment, the reason for determining a fingerprint recognition parameter which matches the characteristic value is that, the fingerprint recognition process may require application of one or more fingerprint recognition parameters, and each fingerprint recognition parameter may be adjusted. For a fingerprint recognition parameter, with a given moisture of the user's finger, the value of the fingerprint recognition parameter may influence the fingerprint recognition performance and result in different fingerprint recognition accuracy. In the embodiment, in order to improve the fingerprint recognition performance, for each one of a plurality of characteristic values, a fingerprint recognition parameter may be determined in advance as corresponding to or matching the characteristic value. The determined fingerprint recognition parameter may be applied under the corresponding condition of user-finger moisture. When a characteristic value is acquired, one or more fingerprint recognition parameters which match the characteristic value may be determined, and the determined one or more fingerprint recognition parameters may be considered as being adapted to the moisture of the user's finger. Therefore, an optimal fingerprint recognition performance may be obtained by applying the determined fingerprint recognition parameters for the fingerprint recognition.

In the related art, the influence of the moisture of the user's finger on fingerprint recognition performance is generally not considered. When the fingerprint image acquired according to the fingerprint signal does not satisfy clarity requirement, the fingerprint recognition parameter may be adjusted, and another fingerprint image is required to be acquired again. These steps are repeated until the acquired fingerprint image satisfies the clarity requirement. Therefore, this traditional approach requires repeatedly acquiring fingerprint images, and has a long processing time for fingerprint recognition. Moreover, the finally acquired fingerprint image may only satisfy the clarity requirement of the fingerprint recognition such that the fingerprint recognition may be implemented, and may not provide an optimal fingerprint recognition performance.

In the device 100 provided by the present disclosure, the influence of the moisture of the user's finger on fingerprint recognition performance is taken into consideration. A characteristic value which is positively related to an impedance value between at least two moisture detection electrodes is acquired, a fingerprint recognition parameter which matches the characteristic value is determined, and fingerprint recognition is performed according to the determined fingerprint recognition parameter and the fingerprint signal. Thereby, the applied fingerprint recognition parameter can match with the moisture of the user's finger. The fingerprint recognition performance and the fingerprint recognition accuracy can be improved. Moreover, the need to repeatedly acquire fingerprint image can be eliminated, thereby significantly reducing time for fingerprint recognition and improving efficiency in fingerprint recognition.

In an embodiment, the moisture of the user's finger may be detected by the fingerprint sensor, to monitor a moisture value of the user's finger. Different software or hardware parameters may be set for different moisture values. Thereby, when performing fingerprint recognition on a current finger, a matched software or hardware parameter may be applied, to achieve an optimal recognition effect and an optimal performance.

In another embodiment, the characteristic value may be acquired by an impedance detection circuit according to an impedance value between the at least two electrodes. For example, the device for recognizing a fingerprint may include an impedance detection circuit. The impedance detection circuit includes at least two input terminals respectively coupled to the at least two moisture detection electrodes 102. The impedance detection circuit is configured to output the characteristic value according to the impedance between the at least two moisture detection electrodes 102, when the user touches the fingerprint sensor 101 and the at least two moisture detection electrodes 102 with a finger.

In an embodiment, the impedance detection circuit may be integrated inside the processing module 103. Alternatively, the impedance detection circuit may be disposed outside the processing module 103. In other words, the at least two moisture detection electrodes 102 are respectively coupled to the at least two input terminals of the impedance detection circuit, and an output terminal of the impedance detection circuit is coupled to the processing module 103.

Figure 3:
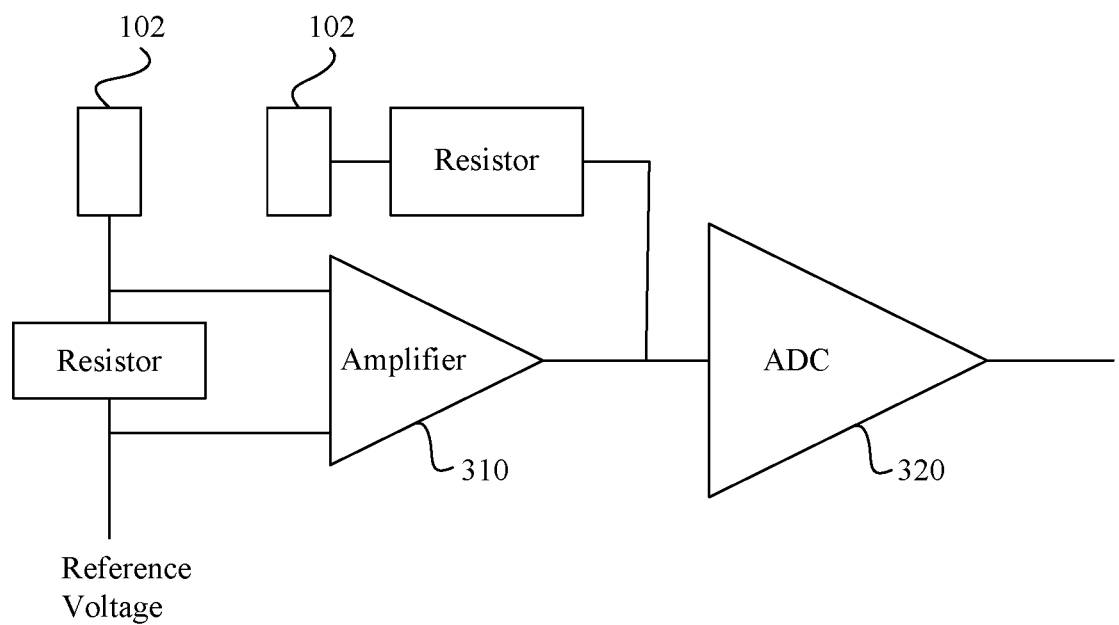
FIG. 3 is a schematic diagram of an impedance detection circuit according to an exemplary embodiment.

In addition, the impedance detection circuit may be implemented in various forms, which are not limited by the embodiments of the present disclosure, as long as the outputted characteristic value is positively related to the impedance between the at least two moisture detection electrodes 102. For example, if there are two moisture detection electrodes 102, the impedance detection circuit may be configured as an impedance detection circuit 300 as shown in FIG. 3, in which, an amplifier feedback circuit 310 may be disposed between the two moisture detection electrodes 102. When the impedance between the two moisture detection electrodes 102 changes, a gain which is fed back may directly influence the voltage outputted by an Analog to Digital Converter (ADC) 320. Therefore, the outputted voltage signal may represent the impedance value between the two moisture detection electrodes 102.

Figure 4:
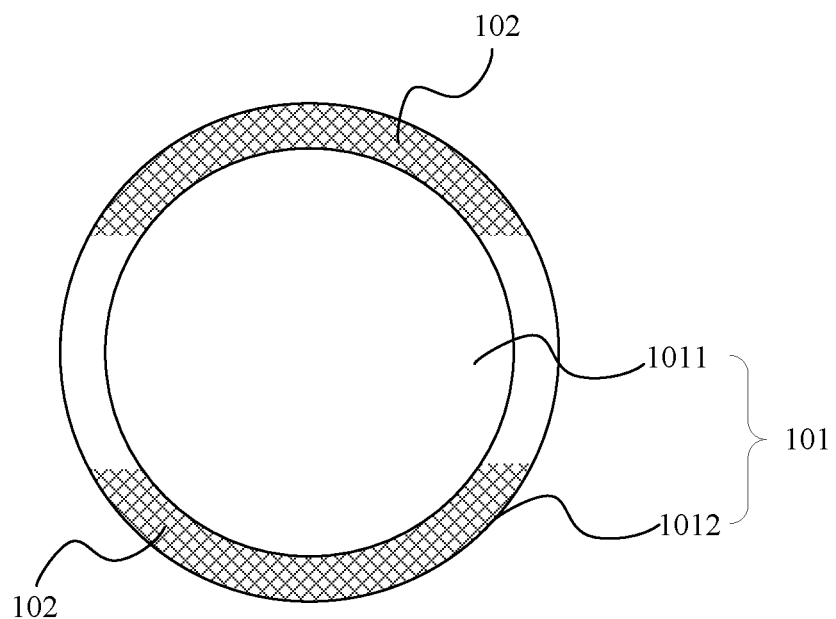
FIG. 4 is a schematic diagram of a fingerprint sensor and two moisture detection electrodes according to an exemplary embodiment.

In another embodiment, shown in FIG. 4, the fingerprint sensor 101 may include a sensing region 1011 and a metal ring 1012. The metal ring 1012 is located outside the sensing region 1011 and surrounds the sensing region 1011. During the process of fingerprint recognition, when the user touches the sensing region 1011 and the metal ring 1012 with a finger, the metal ring 1012 may emit a signal which passes through the user's finger and reaches the sensing region 1011, and the sensing region 1011 may receive a returned signal and may acquire a fingerprint signal according to a difference between the emitted signal and the returned signal.

In the embodiment, the at least two moisture detection electrodes 102 may be disposed on the metal ring 1012. Referring to FIG. 4, as shown by the hatched parts, parts of the metal ring function as the moisture detection electrodes 102 and are coupled to the processing module 103. By reusing an existing metal ring for moisture detection, it can eliminate the need for an additional electrode and can save hardware cost.

Figure 5:
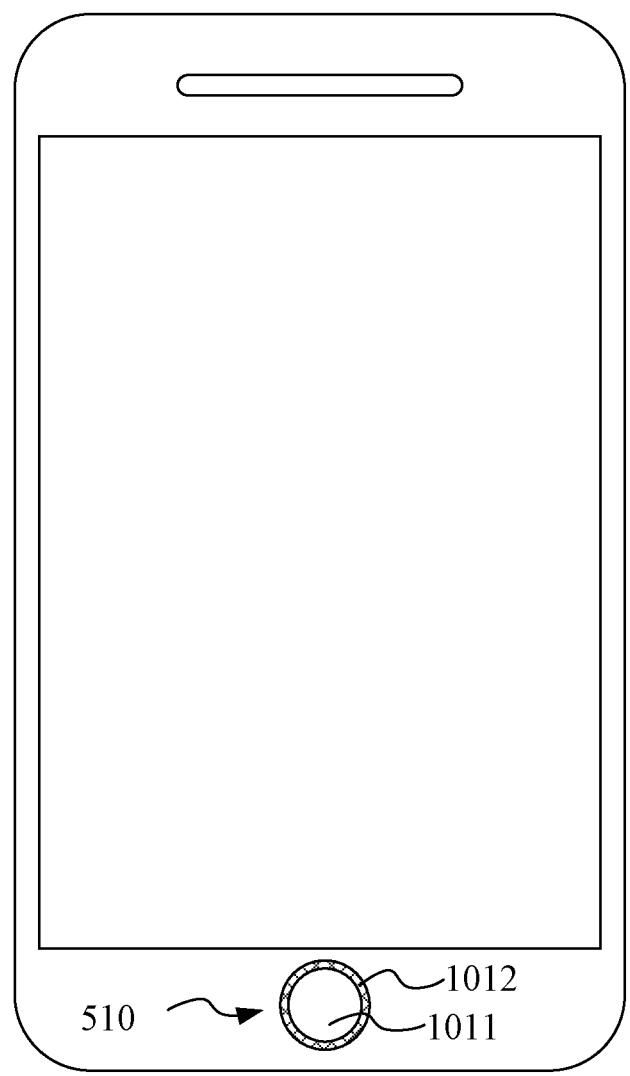
FIG. 5 is a schematic diagram of a button on a mobile phone according to an exemplary embodiment.

The sensing region 1011 and the metal ring 1012 may be disposed on the surface of the housing of the device 100 for recognizing a fingerprint. Referring to FIG. 5, the device for recognizing a fingerprint is a mobile phone 500, for example. A button 510 may be disposed on the housing of the mobile phone 500. The sensing region 1011 and the metal ring 1012 are disposed on the upper surface of the button 510. Parts of the metal ring 1012 may function as moisture detection electrodes. When the user touches the button, a fingerprint signal may be acquired by means of the sensing region 1011. A characteristic value may be acquired by means of the moisture detection electrodes on the metal ring. Then, fingerprint recognition may be performed according to the fingerprint signal and the characteristic value.

In another embodiment, the processing module 103 may determine a preset corresponding relationship in advance. The preset corresponding relationship includes at least one fingerprint recognition parameter for each one of a plurality of characteristic values. Thereby, under the moisture condition corresponding to each characteristic value, a fingerprint recognition parameter may be determined to achieve an optimal fingerprint recognition performance. When the processing module 103 acquires the characteristic value, the processing module 103 may determine a fingerprint recognition parameter which matches the characteristic value according to the preset corresponding relationship.

In an embodiment, the preset corresponding relationship may be predetermined through times of test, to ensure that the fingerprint recognition parameter corresponding to each characteristic value may achieve an optimal fingerprint recognition performance under a corresponding moisture condition.

In an embodiment, after the fingerprint recognition parameter which matches the characteristic value is determined, the processing module 103 may generate a fingerprint image according to the fingerprint recognition parameter and the fingerprint signal, and extract features from the fingerprint image to obtain feature information. Then, the processing module 103 may compare the feature information with previously stored feature information to obtain a fingerprint recognition result.

The fingerprint recognition parameter which matches the characteristic value may be of various types, including software parameters and hardware parameter etc.

In one embodiment, during the process of fingerprint recognition, an Analog to Digital Converter (ADC) may be applied for amplifying a fingerprint signal and generating a fingerprint image to be recognized according to the amplified fingerprint signal. During this process, some parameters relevant to the ADC may influence the performance of the ADC, and in turn, may influence the fingerprint recognition performance. Therefore, in order to improve the fingerprint recognition performance, the preset corresponding relationship may include ADC-relevant parameters respectively matching each characteristic value.

For example, the fingerprint recognition parameter may include at least one of a gain or an operation range of an ADC. Then, a matching fingerprint recognition parameter may be selected according to an acquired characteristic value, and then the ADC may be operated according to the determined fingerprint recognition parameter to achieve a better fingerprint signal, in turn a better fingerprint recognition result and an optimal fingerprint recognition performance. When the characteristic value is relatively small, it means the user's finger has a relatively large moisture. In this case, a relatively large ADC gain may be selected to improve clarity and signal to noise ratio of outputted fingerprint signal. Moreover, a relatively narrow operation range of the ADC may be selected to improve accuracy. On the other hand, when the characteristic value is relatively large, the moisture of the user's finger is relatively small, a relatively small ADC gain and a relatively wide operation range of the ADC may be selected.

In another embodiment, during the process of fingerprint recognition, the processing module 103 may control the fingerprint sensor 101 according to a driving voltage of the ADC. Therefore, the magnitude of the driving voltage may influence the performance of the fingerprint sensor 101 and the fingerprint signal outputted by the fingerprint sensor 101. Then, in order to improve the fingerprint recognition performance, the preset corresponding relationship may include a driving voltage corresponding to each characteristic value. When the characteristic value is relatively small, that is, when the user's finger has a relatively large moisture, a relatively high driving voltage may be selected to enhance the strength of the outputted fingerprint signal. On the other hand, when the characteristic value is relatively large, that is, when the user's finger has a relatively small moisture, a relatively low driving voltage may be selected.

In another embodiment, during the process of fingerprint recognition, a preset algorithm may be applied to process the fingerprint signal to generate a finger image, and another preset algorithm may be applied to recognize the fingerprint image to obtain a fingerprint recognition result. During this process, many parameters may be applied, and they will influence the fingerprint recognition performance. Therefore, in order to improve the fingerprint recognition performance, the preset corresponding relationship may include a fingerprint recognition parameter required by the preset algorithms, which matches each characteristic value.

For example, the fingerprint recognition parameter may include at least one of a scanning frequency, a peak-signal adjustment coefficient, or a trough-signal adjustment coefficient.

The scanning frequency refers to a frequency at which the fingerprint sensor 101 scans the finger of the user to generate a fingerprint signal. The higher the scanning frequency is, the higher the accuracy of the fingerprint recognition will be. Therefore, when the characteristic value is relatively small, that is, when the user's finger has a relatively large moisture, a relatively large scanning frequency may be selected, to improve the accuracy of the fingerprint recognition. When the characteristic value is relatively large, that is, when the user's finger has a relatively small moisture, a relatively lower scanning frequency may be selected.

The peak-signal adjustment coefficient refers to a coefficient for adjusting an acquired peak signal. The trough-signal adjustment coefficient refers to a coefficient for adjusting an acquired trough signal. When the processing module 103 acquires a fingerprint signal, the processing module 103 may distinguish a peak signal from a trough signal, and may adjust the peak signal and the trough signal respectively with different coefficients, to increase the difference between the peak signal and the trough signal. Therefore, when the characteristic value is relatively small, that is, when the user's finger has a relatively large moisture, a relatively large peak-signal adjustment coefficient and a relatively small trough-signal adjustment coefficient may be selected, to increase the difference between the peak signal and the trough signal. On the other hand, when the characteristic value is relatively large, that is, when the user's finger has a relatively small moisture, the peak-signal adjustment coefficient and the trough-signal adjustment coefficient may be selected such that they have a relatively small difference.

The above embodiments may be combined in any manner to form other embodiments of the present disclosure, which will not be elaborated herein.

Figure 6:
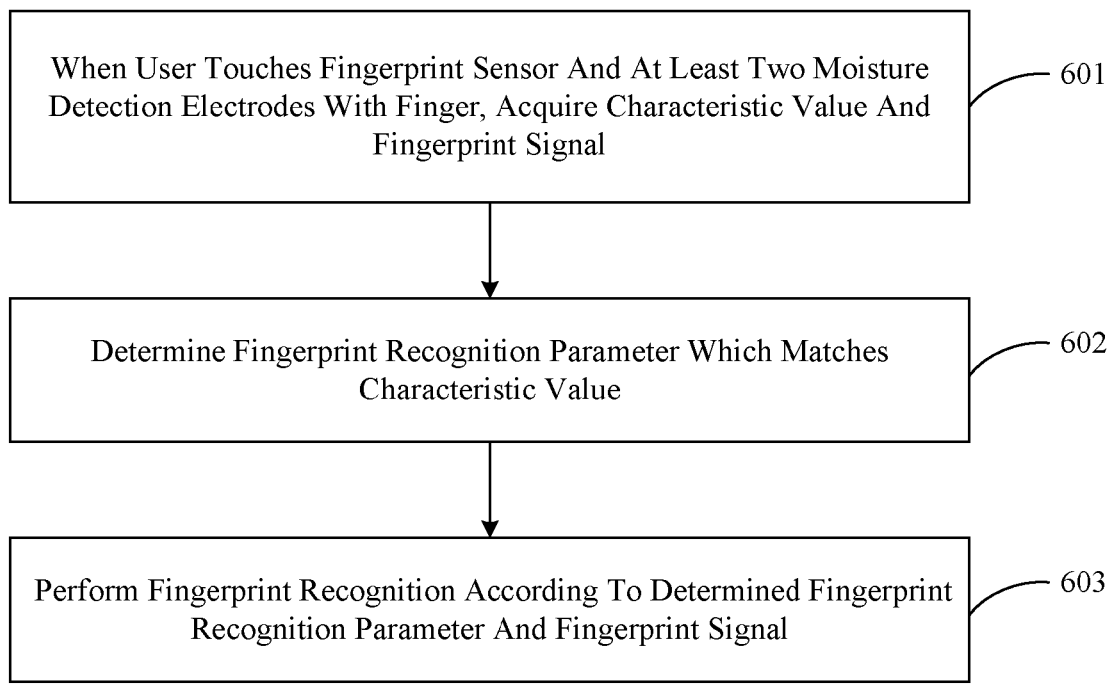
FIG. 6 is a flow chart of a method for recognizing a fingerprint according to an exemplary embodiment.

FIG. 6 is a flow chart illustrating a method 600 for recognizing a fingerprint according to an exemplary embodiment. For example, the method 600 for recognizing a fingerprint is applied in a device for recognizing a fingerprint, the device for recognizing a fingerprint including: a fingerprint sensor, at least two moisture detection electrodes and a processing module. Referring to FIG. 6, the method 600 includes the following steps.

At step 601, a characteristic value and a fingerprint signal are acquired when the user touches the fingerprint sensor and the at least two moisture detection electrodes with a finger. The characteristic value is positively related to an impedance between the at least two moisture detection electrodes.

At step 602, a fingerprint recognition parameter which matches the characteristic value is determined.

At step 603, fingerprint recognition is performed according to the determined fingerprint recognition parameter and the fingerprint signal.

In the method 600, the influence of the moisture of the user's finger on fingerprint recognition performance is taken into consideration. A characteristic value which is positively related to an impedance value between at least two moisture detection electrodes is acquired, a fingerprint recognition parameter which matches the characteristic value is determined, and fingerprint recognition is performed according to the determined fingerprint recognition parameter and the fingerprint signal. Thereby, the applied fingerprint recognition parameter matches the moisture of the user's finger, and the fingerprint recognition performance and the fingerprint recognition accuracy are improved. Moreover, the need to repeatedly acquire fingerprint image can be eliminated, thereby significantly reducing time for fingerprint recognition and improving efficiency in fingerprint recognition.

In another embodiment, determining a fingerprint recognition parameter which matches the characteristic value includes: determining a fingerprint recognition parameter which matches the characteristic value according to a preset corresponding relationship, the preset corresponding relationship including at least one fingerprint recognition parameter which matches each one of a plurality of characteristic values.

In another embodiment, performing fingerprint recognition according to the determined fingerprint recognition parameter and the fingerprint signal includes: generating a fingerprint image according to the fingerprint recognition parameter and the fingerprint signal; extracting features from the fingerprint image to obtain feature information; and comparing the feature information with previously stored feature information.

In another embodiment, the fingerprint recognition parameter includes at least one of a gain, an operation range, or a driving voltage of an Analog to Digital Converter (ADC).

In another embodiment, the fingerprint recognition parameter includes at least one of a scanning frequency, a peak-signal adjustment coefficient, or a trough-signal adjustment coefficient. The peak-signal adjustment coefficient refers to a coefficient for adjusting a peak signal during fingerprint recognition, and the trough-signal adjustment coefficient refers to a coefficient for adjusting a trough signal during fingerprint recognition.

The above embodiments may be combined in any manner to form other embodiments of the present disclosure, which will not be elaborated herein.

Figure 7:
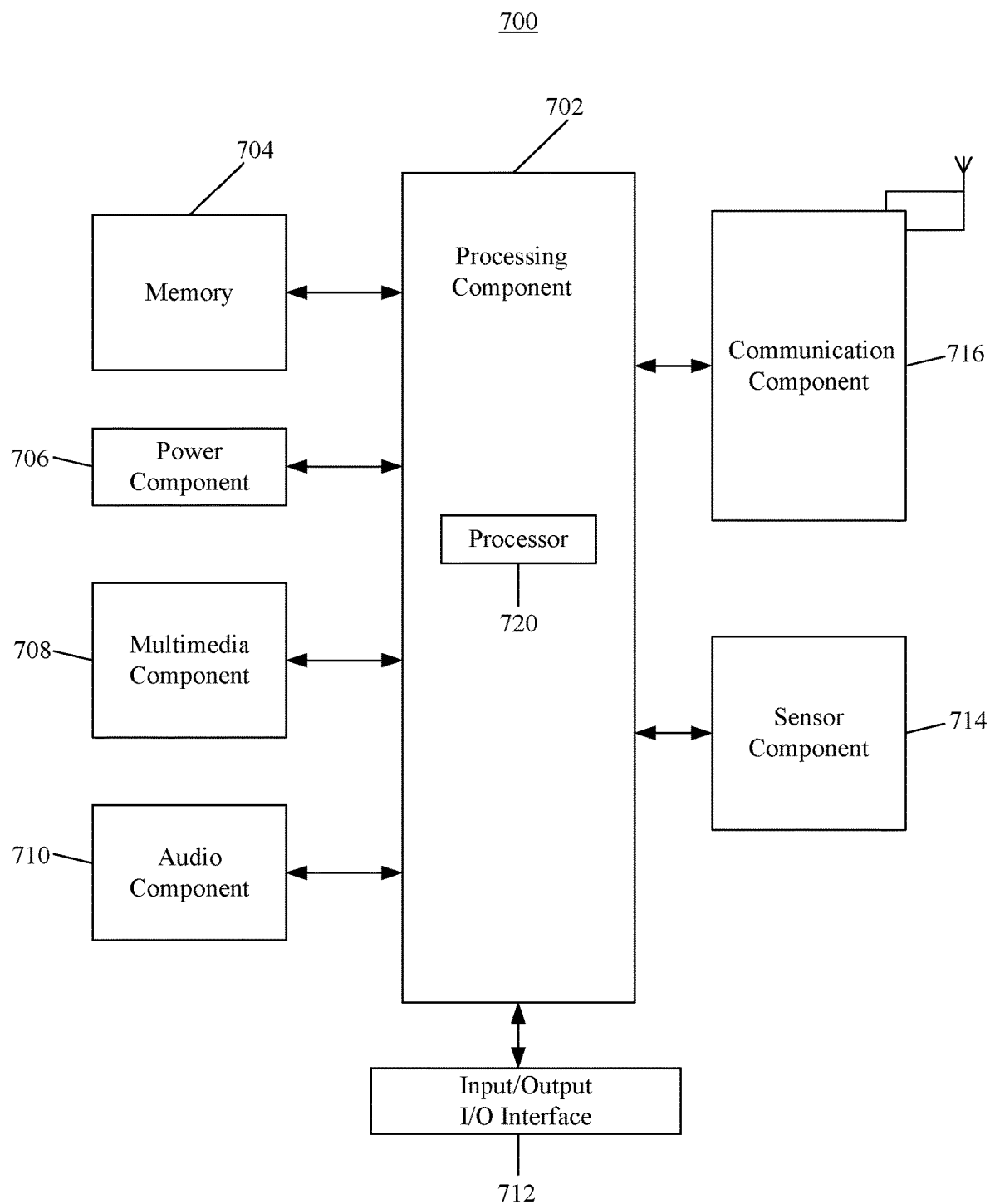
FIG. 7 is a block diagram of a device for recognizing a fingerprint according to an exemplary embodiment.

FIG. 7 is a block diagram of a device 700 for recognizing a fingerprint according to an exemplary embodiment. For example, the device 700 may be a mobile phone, a computer, a digital broadcast terminal, a messaging device, a gaming console, a tablet, a medical device, exercise equipment, a personal digital assistant, and the like.

Referring to FIG. 7, the device 700 can include one or more of the following components: a processing component 702, a memory 704, a power component 706, a multimedia component 708, an audio component 710, an input/output (I/O) interface 712, a sensor component 714, and a communication component 716.

The processing component 702 typically controls overall operations of the device 700, such as the operations associated with display, telephone calls, data communications, camera operations, and recording operations. The processing component 702 can include one or more processors 720 to execute instructions to perform all or part of the steps in the above described methods. Moreover, the processing component 702 can include one or more modules which facilitate the interaction between the processing component 702 and other components. For instance, the processing component 702 can include a multimedia module to facilitate the interaction between the multimedia component 708 and the processing component 702.

The memory 704 is configured to store various types of data to support the operation of the device 700. Examples of such data include instructions for any applications or methods operated on the device 700, contact data, phonebook data, messages, pictures, video, etc. The memory 704 can be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 706 provides power to various components of the device 700. The power component 706 can include a power management system, one or more power sources, and any other components associated with the generation, management, and distribution of power in the device 700.

The multimedia component 708 includes a screen providing an output interface between the device 700 and the user. In some embodiments, the screen can include a liquid crystal display (LCD) and a touch panel. If the screen includes the touch panel, the screen can be implemented as a touch screen to receive input signals from the user. The touch panel includes one or more touch sensors to sense touches, swipes, and gestures on the touch panel. The touch sensors can not only sense a boundary of a touch or swipe action, but also sense a period of time and a pressure associated with the touch or swipe action. In some embodiments, the multimedia component 708 includes a front camera and/or a rear camera. The front camera and the rear camera can receive an external multimedia datum while the device 700 is in an operation mode, such as a photographing mode or a video mode. Each of the front camera and the rear camera can be a fixed optical lens system or have focus and optical zoom capability.

The audio component 710 is configured to output and/or input audio signals. For example, the audio component 710 includes a microphone configured to receive an external audio signal when the device 700 is in an operation mode, such as a call mode, a recording mode, and a voice recognition mode. The received audio signal can be further stored in the memory 704 or transmitted via the communication component 716. In some embodiments, the audio component 710 further includes a speaker to output audio signals.

The I/O interface 712 provides an interface between the processing component 702 and peripheral interface modules, such as a keyboard, a click wheel, buttons, and the like. The buttons can include, but are not limited to, a home button, a volume button, a starting button, and a locking button.

The sensor component 714 includes one or more sensors to provide status assessments of various aspects of the device 700. For instance, the sensor component 714 can detect an open/closed status of the device 700, relative positioning of components, e.g., the display and the keypad of the device 700. The sensor component 714 can also detect a change in position of the device 700 or a component of the device 700, a presence or absence of user contact with the device 700, an orientation or an acceleration/deceleration of the device 700, and a change in temperature of the device 700. The sensor component 714 can include a proximity sensor configured to detect the presence of nearby objects without any physical contact. The sensor component 714 can also include a light sensor, such as a CMOS or CCD image sensor, for use in imaging applications. In some embodiments, the sensor component 714 can also include an accelerometer sensor, a gyroscope sensor, a magnetic sensor, a pressure sensor, or a temperature sensor. In the embodiment, in order to implement fingerprint recognition function, the sensor component 714 includes a fingerprint sensor.

The communication component 716 is configured to facilitate communication, wired or wirelessly, between the device 700 and other devices. The device 700 can access a wireless network based on a communication standard, such as WiFi, 2G; 3G; or 4G; or a combination thereof. In one exemplary embodiment, the communication component 716 receives a broadcast signal or broadcast associated information from an external broadcast management system via a broadcast channel. In one exemplary embodiment, the communication component 716 further includes a near field communication (NFC) module to facilitate short-range communications. For example, the NFC module can be implemented based on a radio frequency identification (RFID) technology, an infrared data association (IrDA) technology, an ultra-wideband (UWB) technology, a Bluetooth (BT) technology, and other technologies.

In exemplary embodiments, the device 700 can be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above described methods.

In exemplary embodiments, there is also provided a non-transitory computer-readable storage medium including instructions, such as included in the memory 704, executable by the processor 720 in the device 700, for performing the above-described methods. For example, the non-transitory computer-readable storage medium can be a ROM, a RAM, a CD-ROM, a magnetic tape, a floppy disc, an optical data storage device, and the like.

In exemplary embodiments, there is also provided a non-transitory computer-readable storage medium. When instructions in the storage medium are executed by a processor of a terminal, the terminal is caused to perform the above-described methods for recognizing a fingerprint.

One of ordinary skill in the art will understand that the above described modules can each be implemented by hardware, or software, or a combination of hardware and software. One of ordinary skill in the art will also understand that multiple ones of the above described modules may be combined as one module, and each of the above described modules may be further divided into a plurality of submodules.

Other embodiments of the invention will be apparent to those skilled in the art from consideration of the specification and practice of the invention disclosed here. This application is intended to cover any variations, uses, or adaptations of the invention following the general principles thereof and including such departures from the present disclosure as come within known or customary practice in the art. It is intended that the specification and examples be considered as exemplary only, with a true scope and spirit of the invention being indicated by the following claims.

It will be appreciated that the present invention is not limited to the exact construction that has been described above and illustrated in the accompanying drawings, and that various modifications and changes can be made without departing from the scope thereof. It is intended that the scope of the invention only be limited by the appended claims.

What is claimed is:

1. A device for recognizing a fingerprint, comprising:
   a fingerprint sensor;
   at least two moisture detection electrodes disposed within a preset range of the fingerprint sensor; and
   a processor coupled to the fingerprint sensor and the at least two moisture detection electrodes, wherein,
   the fingerprint sensor is configured to output a fingerprint signal to the processor when a user touches the fingerprint sensor and the at least two moisture detection electrodes with a finger, and the fingerprint sensor includes an Analog to Digital Converter (ADC) configured to amplify the fingerprint signal;
   the processor is configured to:
      acquire a characteristic value which is positively related to an impedance between the at least two moisture detection electrodes when the user touches the fingerprint sensor and the at least two moisture detection electrodes with the finger;
      determine a fingerprint recognition parameter which matches the characteristic value; and
      perform fingerprint recognition according to the determined fingerprint recognition parameter and the fingerprint signal,
   wherein the fingerprint recognition parameter comprises an operation range of the ADC, and
   wherein the performing fingerprint recognition according to the determined fingerprint recognition parameter and the fingerprint signal comprises applying the ADC to amplify the fingerprint signal and generating a fingerprint image to be recognized according to the fingerprint signal amplified.

2. The device of claim 1, further comprising an impedance detection circuit,
   wherein the at least two moisture detection electrodes are respectively coupled to at least two input terminals of the impedance detection circuit, and
   the impedance detection circuit is configured to output the characteristic value according to the impedance between the at least two moisture detection electrodes, when the user touches the fingerprint sensor and the at least two moisture detection electrodes with the finger.

3. The device of claim 1, wherein the fingerprint sensor is provided with a metal ring, and the at least two moisture detection electrodes are disposed on the metal ring.

4. The device of claim 1, wherein the processor is configured to determine the fingerprint recognition parameter which matches the characteristic value according to a preset corresponding relationship, and the preset corresponding relationship comprises at least one fingerprint recognition parameter which matches each one of a plurality of characteristic values.

5. The device of claim 1, wherein the processor is further configured to:
   generate the fingerprint image according to the fingerprint recognition parameter and the fingerprint signal;
   extract features from the fingerprint image to obtain feature information; and
   compare the feature information with previously stored feature information.

6. The device of claim 1, wherein the fingerprint recognition parameter comprises at least one of a scanning frequency, a peak-signal adjustment coefficient, or a trough-signal adjustment coefficient, the peak-signal adjustment coefficient being a coefficient for adjusting an acquired peak signal, and the trough-signal adjustment coefficient being a coefficient for adjusting an acquired trough signal.

7. A method for recognizing a fingerprint, which is applied in a device including a fingerprint sensor which includes an Analog to Digital Converter (ADC), at least two moisture detection electrodes, and a processor, the method comprising:
   acquiring a characteristic value and a fingerprint signal when a user touches the fingerprint sensor and the at least two moisture detection electrodes with a finger, the characteristic value being positively related to an impedance between the at least two moisture detection electrodes;
   determining a fingerprint recognition parameter which matches the characteristic value; and
   performing fingerprint recognition according to the determined fingerprint recognition parameter and the fingerprint signal,
   wherein the fingerprint recognition parameter comprises an operation range of the ADC,
   wherein the performing fingerprint recognition according to the determined fingerprint recognition parameter and the fingerprint signal comprises applying the ADC to amplify the fingerprint signal and generating a fingerprint image to be recognized according to the fingerprint signal amplified.

8. The method of claim 7, wherein determining the fingerprint recognition parameter which matches the characteristic value comprises:
   determining the fingerprint recognition parameter which matches the characteristic value according to a preset corresponding relationship, the preset corresponding relationship comprising at least one fingerprint recognition parameter which matches each one of a plurality of characteristic values.

9. The method of claim 7, wherein performing fingerprint recognition according to the determined fingerprint recognition parameter and the fingerprint signal comprises:
   generating the fingerprint image according to the fingerprint recognition parameter and the fingerprint signal;
   extracting features from the fingerprint image to obtain feature information; and
   comparing the feature information with previously stored feature information.

10. The method of claim 7, wherein the fingerprint recognition parameter comprises at least one of a scanning frequency, a peak-signal adjustment coefficient, or a trough-signal adjustment coefficient, the peak-signal adjustment coefficient being a coefficient for adjusting a peak signal during fingerprint recognition, and the trough-signal adjustment coefficient being a coefficient for adjusting a trough signal during fingerprint recognition.

11. A non-transitory computer-readable storage medium having stored therein instructions that, when executed by a processor of a terminal, cause the terminal to perform a method for recognizing a fingerprint, the method comprising:

acquiring a characteristic value and a fingerprint signal when a user touches a fingerprint sensor and at least two moisture detection electrodes with a finger, the characteristic value being positively related to an impedance between the at least two moisture detection electrodes;

determining a fingerprint recognition parameter which matches the characteristic value; and performing fingerprint recognition according to the determined fingerprint recognition parameter and the fingerprint signal, wherein the fingerprint recognition parameter comprises an operation range of an Analog to Digital Converter (ADC) included in the fingerprint sensor, wherein the performing fingerprint recognition according to the determined fingerprint recognition parameter and the fingerprint signal comprises applying the ADC to amplify the fingerprint signal and generating a fingerprint image to be recognized according to the fingerprint signal amplified.

12. The non-transitory computer-readable storage medium of claim 11, wherein determining the fingerprint recognition parameter which matches the characteristic value comprises:

determining the fingerprint recognition parameter which matches the characteristic value according to a preset corresponding relationship, the preset corresponding relationship comprising at least one fingerprint recognition parameter which matches each one of a plurality of characteristic values.

13. The non-transitory computer-readable storage medium of claim 11, wherein performing fingerprint recognition according to the determined fingerprint recognition parameter and the fingerprint signal comprises:

generating the fingerprint image according to the fingerprint recognition parameter and the fingerprint signal;

extracting features from the fingerprint image to obtain feature information; and comparing the feature information with previously stored feature information.

14. The non-transitory computer-readable storage medium of claim 11 wherein the fingerprint recognition parameter comprises at least one of a scanning frequency, a peak-signal adjustment coefficient, or a trough-signal adjustment coefficient, the peak-signal adjustment coefficient being a coefficient for adjusting a peak signal during fingerprint recognition, and the trough-signal adjustment coefficient being a coefficient for adjusting a trough signal during fingerprint recognition.

* * * * *